(12) United States Patent
Lewis

(10) Patent No.: US 7,337,684 B1
(45) Date of Patent: Mar. 4, 2008

(54) TOOL FOR REMOVING SURFACE MATERIAL

(76) Inventor: Nicholas J. Lewis, 12 Faraday Avenue, Sidcup (GB) UK2 DA14 4JD ( * ) Notice: Subject to any disclaimer, the term of this patent is extended or adjusted under 35 U.S.C. 154(b) by 358 days.

(21) Appl. No.: 11/124,514

(22) Filed: May 9, 2005

(51) Int. Cl.
*G01N 1/08* (2006.01)

(52) U.S. Cl. .................................. 73/864.41

(58) Field of Classification Search .............................. 73/864.43–864.45, 864.41; 83/919
See application file for complete search history.

(56) References Cited

U.S. PATENT DOCUMENTS

| | | | |
|---|---|---|---|
| 1,927,871 A * | 9/1933 | Irwin et al. ............... | 73/864.43 |
| 2,435,608 A * | 2/1948 | Sanford et al. ........... | 73/864.43 |
| 2,800,060 A * | 7/1957 | Chapman .................. | 409/110 |
| 3,375,743 A * | 4/1968 | Levy ......................... | 83/919 X |
| 4,276,778 A * | 7/1981 | Ham .......................... | 73/864.43 |
| 4,398,412 A * | 8/1983 | Huneidi .................... | 73/864.41 X |
| 4,812,700 A | 3/1989 | Natale | |
| 4,883,329 A | 11/1989 | Flannery et al. | |
| 4,887,413 A * | 12/1989 | Tuckey, Jr. ............... | 73/864.44 X |
| 4,911,191 A | 3/1990 | Bain | |
| 5,032,328 A | 7/1991 | Griffis | |
| 5,047,207 A * | 9/1991 | Lankow et al. .......... | 73/864.41 X |
| 5,080,701 A | 1/1992 | Howard et al. | |
| D340,332 S | 10/1993 | Davis et al. | |
| 5,833,928 A * | 11/1998 | Ratajczak et al. ....... | 73/864.41 X |
| 5,907,110 A * | 5/1999 | Garcia et al. ............ | 73/864.43 X |
| 6,578,439 B2 * | 6/2003 | Knothe ..................... | 73/864.41 |
| 6,810,728 B1 * | 11/2004 | Kasture et al. .......... | 73/864.41 X |
| 2003/0015044 A1 * | 1/2003 | Knothe ..................... | 73/864.41 |

FOREIGN PATENT DOCUMENTS

JP 55033653 A * 3/1980 .............. 73/864.44

* cited by examiner

*Primary Examiner*—Thomas P. Noland

(57) ABSTRACT

A tool for removing surface material to be analyzed includes a container having an opening therein defined by a peripheral edge. A flexible band is attached to and extends along the peripheral edge. An adhesive coating is positioned on the band. A ring is positioned in a wall of the container. The ring defines an aperture extending through the container. A cutting tool extends through the ring such that a cutting member of the cutting tool is extendable through the opening. The adhesive on the band may be attached to a wall surface such that the cutting tool may scrap the wall surface. Material freed from the wall surface by the cutting tool is captured in the container.

6 Claims, 7 Drawing Sheets

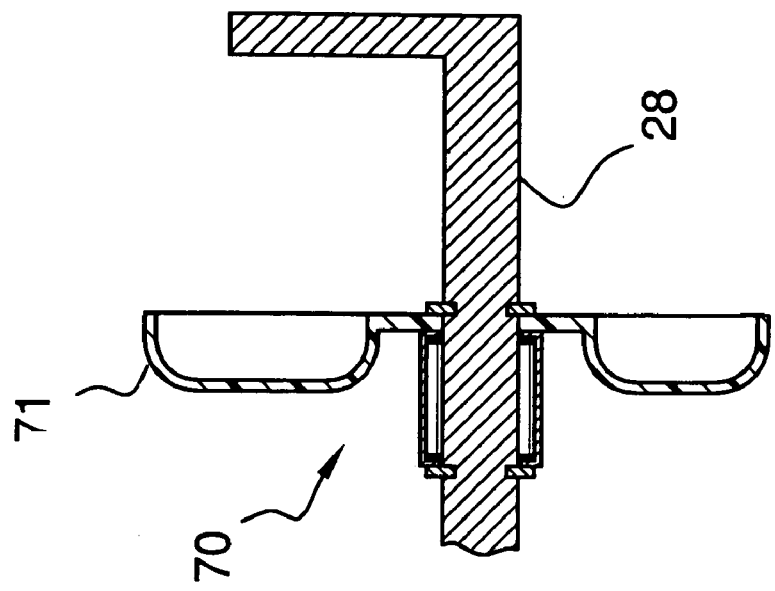
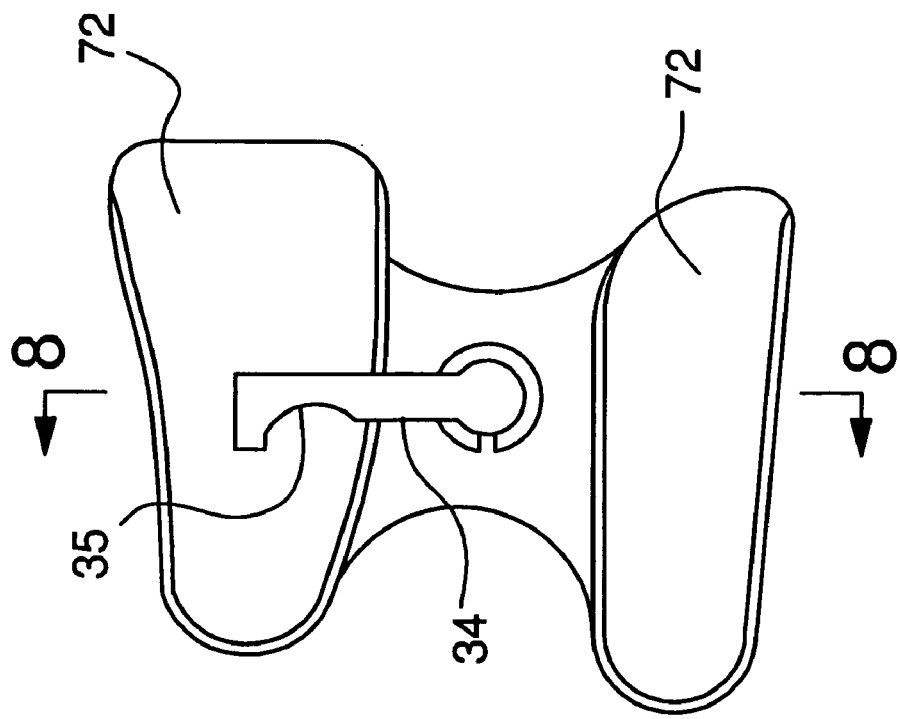

US 7,337,684 B1

TOOL FOR REMOVING SURFACE MATERIAL

BACKGROUND OF THE INVENTION

1. Field of the Invention

The present invention relates to material collection devices and more particularly pertains to a new material collection device for collecting potentially hazardous material from a wall surface.

2. Description of the Prior Art

The use of material collection devices is known in the prior art. However, such devices are often complicated to use and are bulky in their nature. While these devices fulfill their respective, particular objectives and requirements, the need remains for a device that includes a kit for removing a small sample of material without contaminating an area.

SUMMARY OF THE INVENTION

The present invention meets the needs presented above including container having an opening therein defined by a peripheral edge. A flexible band is attached to and extends along the peripheral edge. An adhesive coating is positioned on the band. A ring is positioned in a wall of the container. The ring defines an aperture extending through the container. A cutting tool extends through the ring such that a cutting member of the cutting tool is extendable through the opening.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 7 is a front view of the gripping member of the present invention.

FIG. 8 is a cross-sectional view taken along line 8-8 of FIG. 7 of the present invention.

DESCRIPTION OF THE PREFERRED EMBODIMENT

Figure 1:
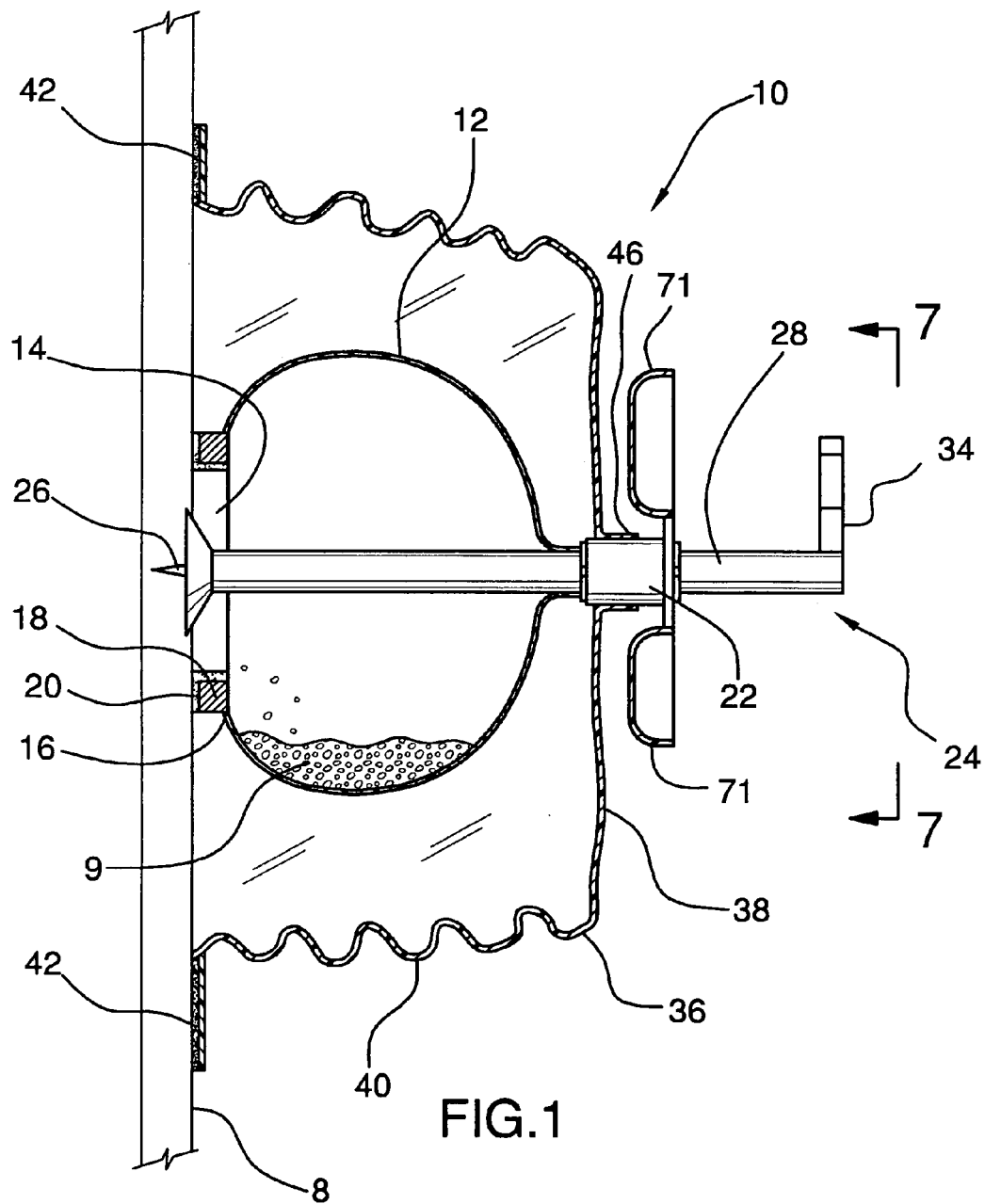
FIG. 1 is a schematic cross-sectional view of a tool for removing surface material according to the present invention.
Figure 2:
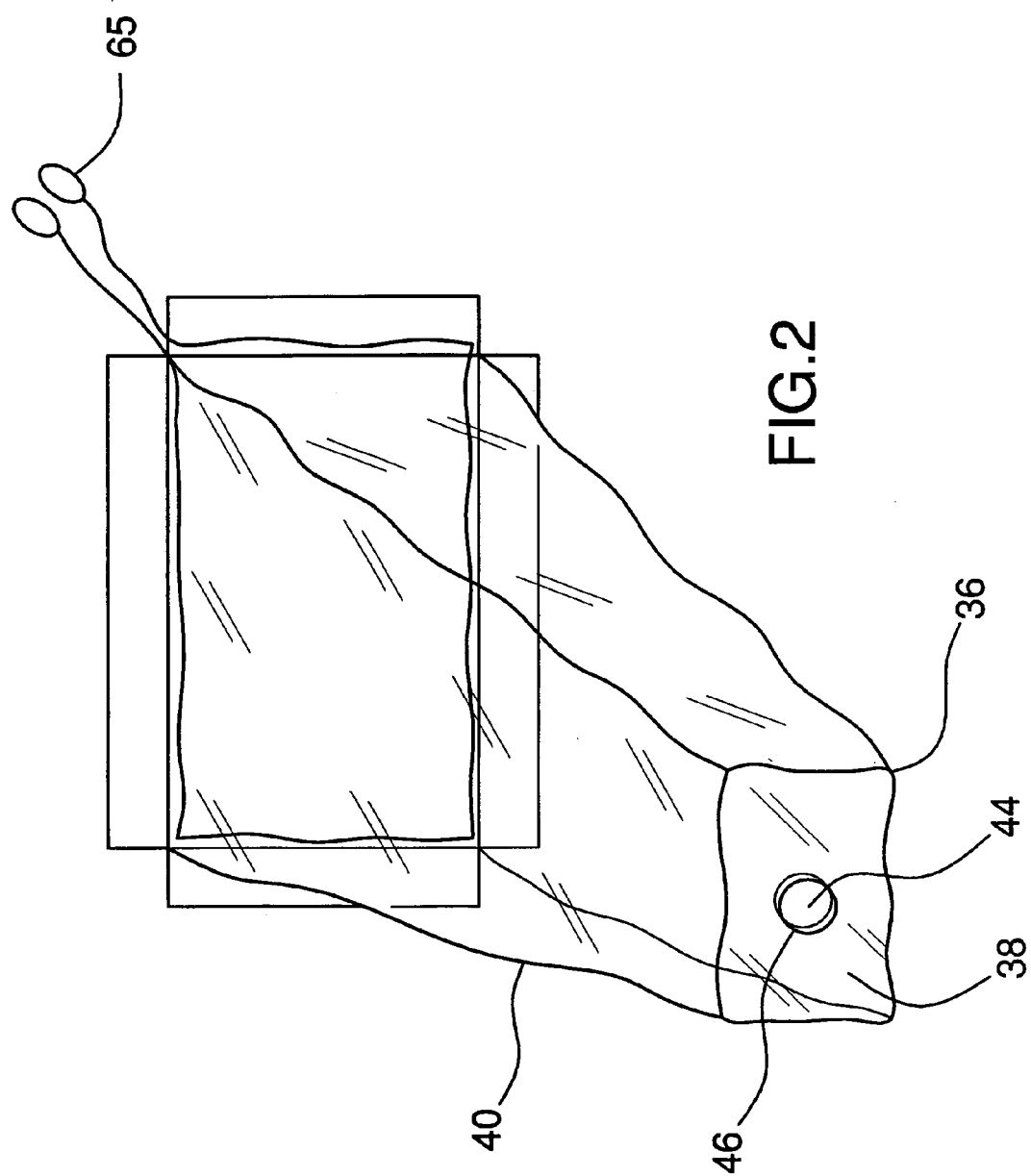
FIG. 2 is a schematic perspective view of a covering of the present invention.

With reference now to the drawings, and in particular to FIGS. 1 through 6 thereof, a new material collection device embodying the principles and concepts of the present invention and generally designated by the reference numeral 10 will be described.

As best illustrated in FIGS. 1 through 6, the tool for removing surface material 10 generally comprises a container 12 having an opening 14 therein defined by a peripheral edge 16. A flexible band 18 is attached to and extends along the peripheral edge 16. An adhesive coating 20 is positioned on the band 18. The coating preferably extends inward toward an interior of the container 12. The container 12 preferably comprises a flexible, clear plastic material.

A ring 22 is positioned in a wall of the container 12. The ring 22 defines an aperture extending through the container 12.

A cutting tool 24 extends through the ring 22 such that a cutting member 26 of the cutting tool 24 is extendable through the opening 14. The cutting tool 24 includes an elongated rod 28 having first end 30 and a second end 32. The cutting member 26 is attached to the first end 30. The cutting member 26 may be any type of blade or threaded member for removing surface material from a wall surface 8. The rod 28 extends through the ring 22 such that the second end 32 of the rod 28 extends away from the container 12. A handle 34 is attached to the second end 32 of the rod 28.

A covering 36 includes an end wall 38 and a peripheral wall 40 that is attached to and extends away from the end wall 38. An adhesive 42 is attached to and extends along a length of a terminal end of the peripheral wall 40 disposed opposite of the end wall 38. The end wall 38 has a hole 44 extending therethrough. The hole 44 is defined by a perimeter edge 46 which is preferably attached to the ring 22. The covering 36 preferably comprises a flexible and clear plastic material so that the user may easily see the task they are performing. Excess material 65 may be added to perimeter edge which may be tied into a knot to close the hole 44. Also, a drawstring 71 may be positioned around the peripheral wall 40 and near the adhesive 42 for closing peripheral wall around the container 12 after a sample has been taken.

A sealed bag 48 comprising a plastic material includes a brush therein 50. A breakable capsule 52 is attached to an inner surface of the sealed bag 48. A liquid clear coat covering material is positioned in the capsule 52. The clear coat material is preferably a clear varnish material though any type of sealant may be used. The sealed bag 48 may be opened and the capsule 52 punctured with the brush 50 such that bristles 54 on the brush 50 are covered with the clear coat covering.

Figure 3:
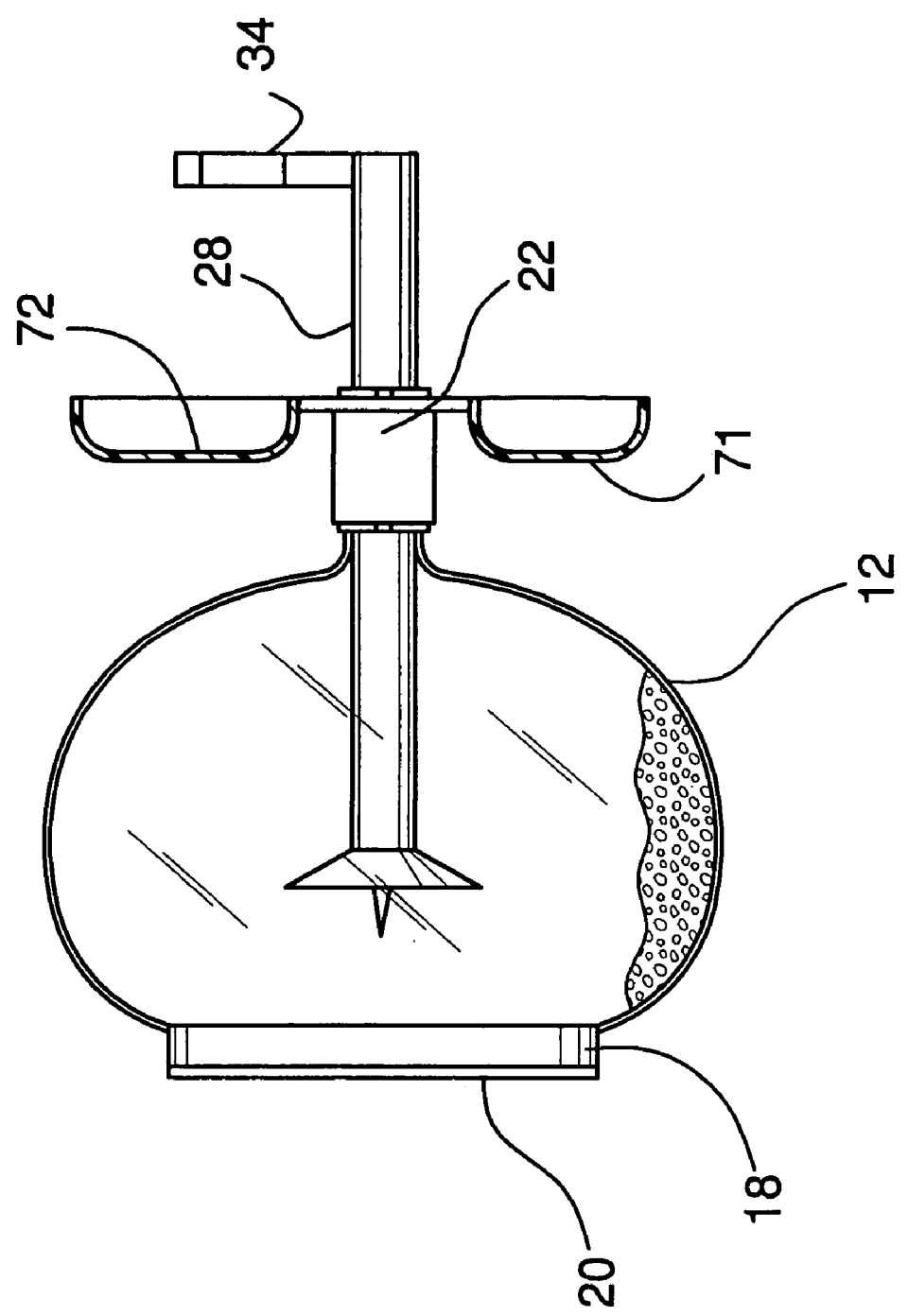
FIG. 3 is a schematic side view of a container and cutting member of the present invention in an open position.
Figure 4:
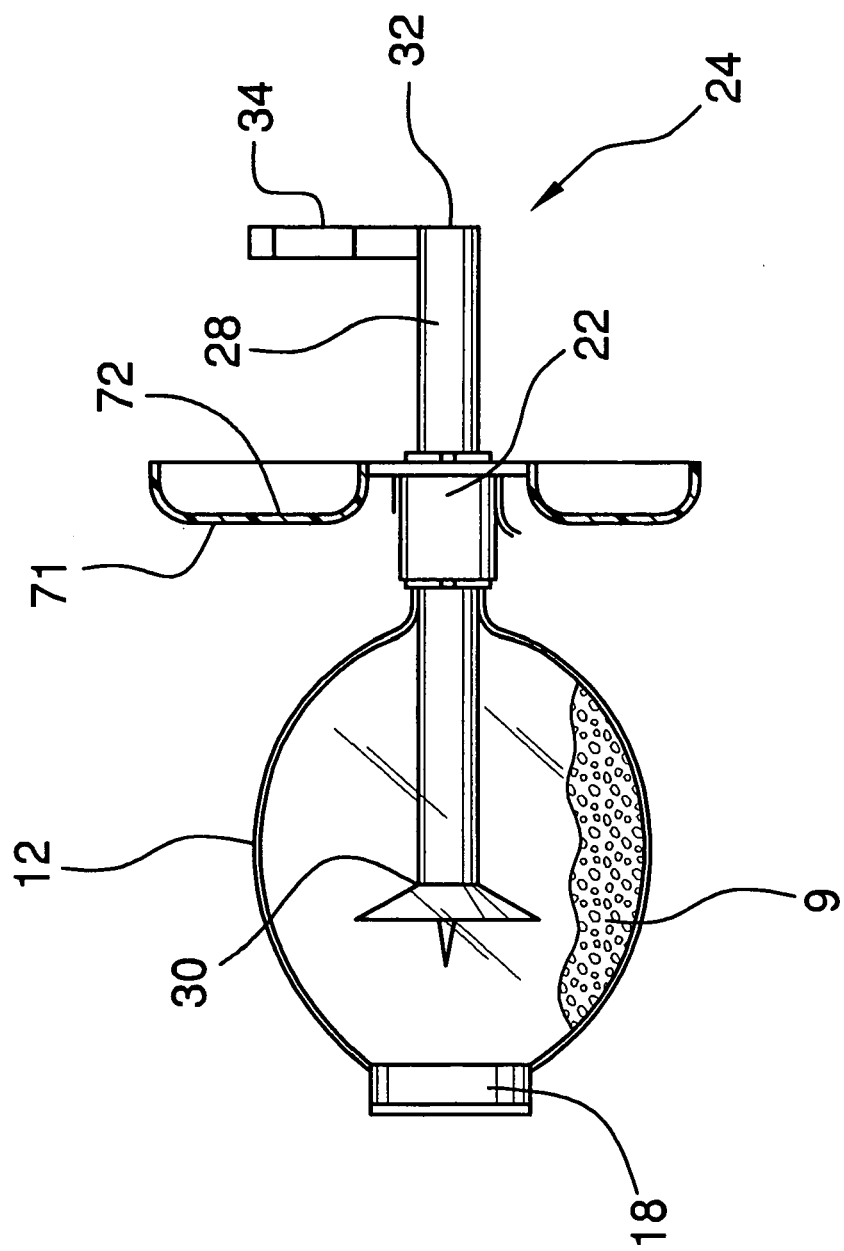
FIG. 4 is a schematic side view of the container and cutting member of the present invention in a closed position.
Figure 5:
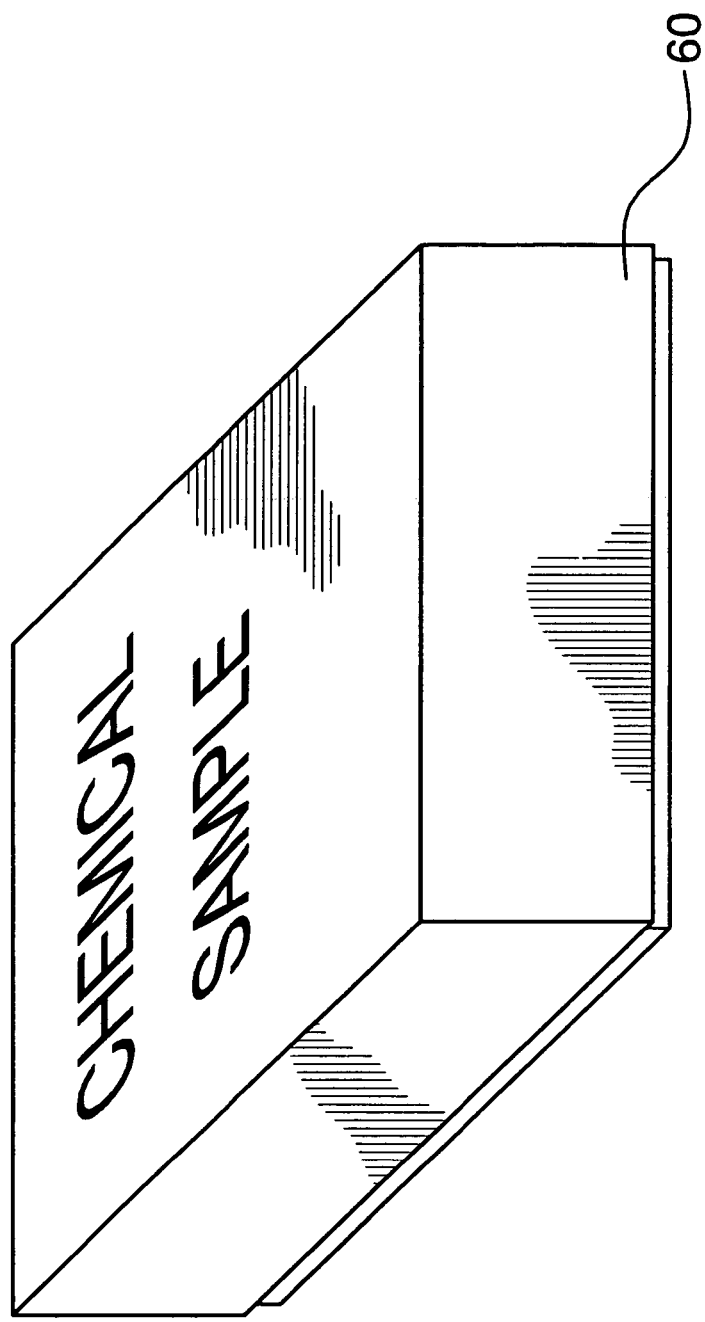
FIG. 5 is a schematic perspective view of a material holding box of the present invention.
Figure 6:
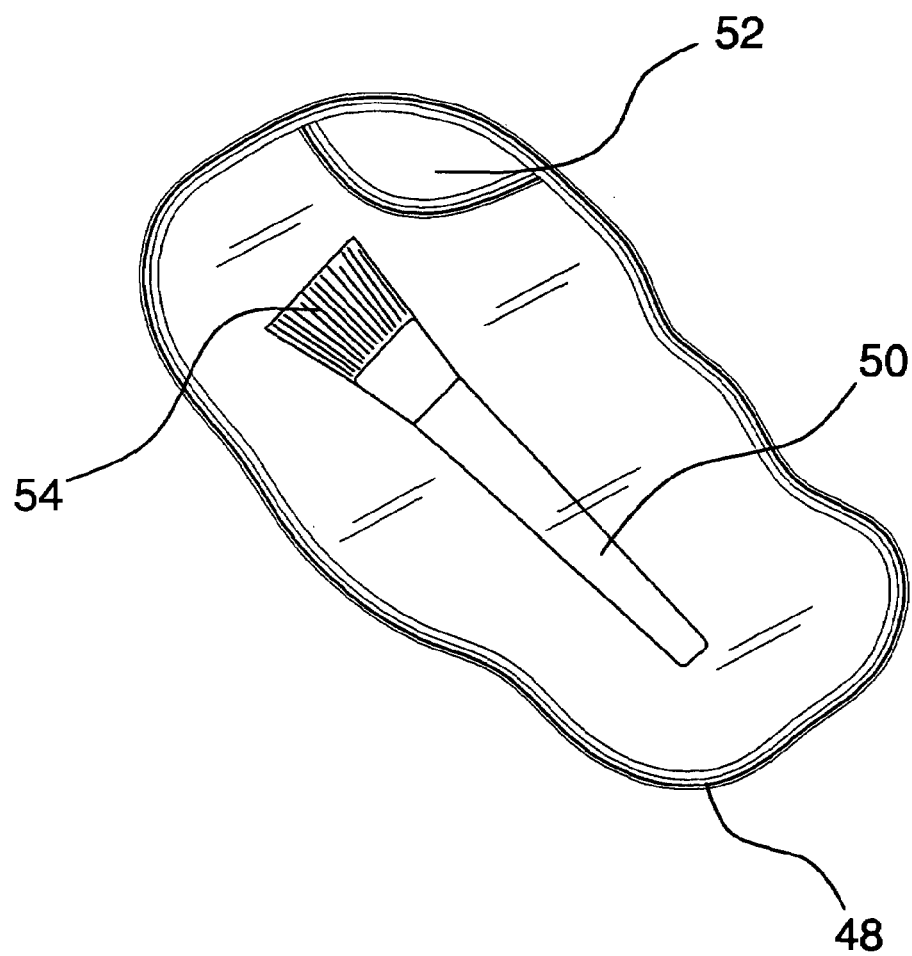
FIG. 6 is a schematic side view of a brush and sealed bag of the present invention

In use, the adhesive 20 on the band 18 may be attached to a wall surface 8 such that the cutting tool 24 may scrap the wall surface 8 at a point desired by the user. The adhesive 42 on the covering 36 is also attached to the wall 8 so that that the covering 36 encapsulates the container 12 as depicted on FIG. 1. FIG. 3 depicts the container 12 without the covering 36. Material 9 freed from the wall surface 8 by the cutting tool 24 is captured in the container 12. The band 18 is then sealed on itself as shown in FIG. 4, again without the covering 36, and the adhesive 42 attached to the covering 36 may also be attached to itself at this time so that the container 12 is sealed within the covering 36. The clear coat material is used to cover the area scraped to seal the area to prevent dispersion of additional material. Ideally, a sample box 60 is provided into the sealed container 12, including the tool 24, and covering 36 may be placed therein for shipment to a laboratory for analysis of the material.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A tool for removing a sample of wall surface material, said tool comprising:
    a container having an opening therein defined by a peripheral edge, a flexible band being attached to and extending along said peripheral edge, an adhesive coating being positioned on said band;
    a ring being positioned in a wall of said container, said ring defining an aperture extending through said container;
    a cutting tool extending through said ring such that a cutting member of said cutting tool is extendable through said opening.

2. The tool of claim 1, wherein said cutting tool includes an elongated rod having first end and a second end, said cutting member being attached to said first end, said rod extending through said ring such that said second end of said rod extends away from said container.

3. The tool of claim 2, further including a handle being attached to said second end of said rod.

4. The tool of claim 1, further including a covering including an end wall and a peripheral wall being attached to and extending away from said end wall, an adhesive being attached to and extending along a length of a terminal end of said peripheral wall disposed opposite of said end wall, said end wall having a hole extending therethrough, said hole being defined by a perimeter edge, said perimeter edge being attached to said ring.

5. The tool of claim 1, further including a sealed bag comprising a plastic material, a brush being positioned within said sealed bag, a capsule being attached to an inner surface of said sealed bag, a liquid clear coat covering material being positioned in said capsule, wherein said sealed bag may be opened and said capsule punctured with said brush such that bristles on said brush are covered with said clear coat covering.

6. A tool for removing a sample of wall surface material, said tool comprising:
    a container having an opening therein defined by a peripheral edge, a flexible band being attached to and extending along said peripheral edge, an adhesive coating being positioned on said band;
    a ring being positioned in a wall of said container, said ring defining an aperture extending through said container;
    a cutting tool extending through said ring such that a cutting member of said cutting tool is extendable through said opening, said cutting tool including an elongated rod having first end and a second end, said cutting member being attached to said first end, said rod extending through said ring such that said second end of said rod extends away from said container, a handle being attached to said second end of said rod;
    a covering including an end wall and a peripheral wall being attached to and extending away from said end wall, an adhesive being attached to and extending along a length of a terminal end of said peripheral wall disposed opposite of said end wall, said end wall having a hole extending therethrough, said hole being defined by a perimeter edge, said perimeter edge being attached to said ring;
    a sealed bag comprising a plastic material, a brush being positioned within said sealed bag, a capsule being attached to an inner surface of said sealed bag, a liquid clear coat covering material being positioned in said capsule, wherein said sealed bag may be opened and said capsule punctured with said brush such that bristles on said brush are covered with said clear coat covering; and
    wherein said adhesive on said band may be attached to a wall surface such that said cutting tool may scrape the wall surface, wherein material freed from the wall surface by said cutting tool is captured in said container.

* * * * *